United States Patent [19]

Norris et al.

[11] Patent Number: 5,306,732
[45] Date of Patent: Apr. 26, 1994

[54] TUMOR NECROSIS FACTOR ANTAGONIST

[75] Inventors: David B. Norris; Paul Depledge, both of Slough; Andrew P. Jackson, Birstall, all of United Kingdom

[73] Assignee: Xenova Limited, Slough, United Kingdom

[21] Appl. No.: 862,574

[22] PCT Filed: Nov. 22, 1990

[86] PCT No.: PCT/GB90/01801
§ 371 Date: Jun. 24, 1992
§ 102(e) Date: Jun. 24, 1992

[87] PCT Pub. No.: WO91/07953
PCT Pub. Date: Jun. 13, 1991

[30] Foreign Application Priority Data

Nov. 24, 1989 [GB] United Kingdom ............. 8926611.8

[51] Int. Cl.$^5$ .......................................... A61K 31/045
[52] U.S. Cl. ................................................... 514/729
[58] Field of Search ........................................ 514/729

[56] References Cited

FOREIGN PATENT DOCUMENTS 0341558 11/1989 European Pat. Off. .

OTHER PUBLICATIONS

The Journal of Antibiotics, vol. XLI, No. 1, 1988, Takeshi Ando et al.: "Vinigrol, a novel antihypertensive and platelet aggregation inhibitory agent produced by a fungus, Virgaria Nigra", pp. 25-30.

Nature, vol. 330, Dec. 17, 1987, K. J. Tracey et al.: "Anti-cachectin/TNF monoclonal antibodies prevent septic shock during lethal bacteraemic", pp. 662-664.

*Primary Examiner*—Jerome D. Goldberg
*Attorney, Agent, or Firm*—Morrison & Foerster

[57] ABSTRACT

Vinigrol or a pharmaceutically acceptable salt thereof is useful as a tumour necrosis factor antagonist. Vinigrol may therefore be used to treat endotoxic shock, inflammation, infection or cachexia.

2 Claims, No Drawings

TUMOR NECROSIS FACTOR ANTAGONIST

The present invention relates to a tumour necrosis factor (TNF) antagonist. TNF is a mediator in the immune system.

Vinigrol is a known compound. It was purified from a culture of the fungus *Virgaria nigra* by Fujisawa Pharmaceutical company Limited, who also described antihypertensive and platelet aggregation inhibitory properties of the compound. The preparation and some pharmacological actions of vinigrol are described by Ando et al, J. Antibiotics XLI, 25-30 (1988) and Ando et al, J. Antibiotics XLI, 31-35 (1988). The structure of vinigrol has been reported by Uchida et al, J. Org. Chem. 52, 529203 (1987) and is:

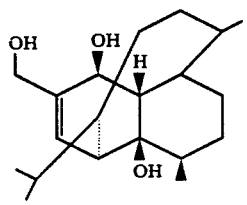

We have now found that vinigrol is a TNF antagonist. Vinigrol or one of its pharmaceutically acceptable salts may therefore be used to treat endotoxic shock, inflammation, infection or cachexia.

Accordingly, the present invention provides the use of vinigrol or a pharmaceutically acceptable salt thereof in the preparation of a medicament for use as a TNF antagonist. An agent for use as a TNF antagonist according to the invention therefore comprises vinigrol or a pharmaceutically acceptable salt thereof.

A patient is treated according to the present invention by a method comprising administering to the patient an effective amount of vinigrol or a pharmaceutically acceptable salt of vinigrol. In this way, vinigrol or the vinigrol salt can be used to control conditions attributable to TNF such as endotoxic shock, inflammation, infection and cachexia.

The vinigrol or vinigrol salt can be administered in a variety of dosage forms, for example orally such as in the form of tablets, capsules, sugar- or film-coated tablets, liquid solutions or suspensions or parenterally, for example intramuscularly, intravenously or subcutaneously. The vinigrol or vinigrol salt may therefore be given by injection or infusion.

The dosage depends on a variety of factors including the age, weight and condition of the patient and the route of administration. Typically, however, the dosage adopted for each route of administration to adult humans is 0.001 to 10 mg/kg body weight. Such a dosage may be given from 1 to 5 times daily.

Vinigrol or a vinigrol salt are formulated for use as a pharmaceutical composition also comprising a pharmaceutically acceptable carrier or diluent. The pharmaceutical compositions are typically prepared following conventional methods and are administered in a pharmaceutically suitable form.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disaggregating agents such as a starch, alginic acid, alginates or sodium starch glycolate; effervescing mixtures; dye-stuffs; sweeteners; wetting agents such as lecithin, polysorbates, laurylsulphates. Such pharmaceutical preparations may be manufactured in known manner, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerine and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Solutions for intravenous injection or infusion may contain as carrier, for example, sterile water which is generally Water for Injections. Preferably, however, they may take the form of a sterile, aqueous, isotonic saline solution.

The following Examples illustrate the invention.

EXAMPLE 1: TNF-receptor binding assay

An in-vitro binding assay, based upon the measurement of binding of $[^{125}I]$-TNF to intact cells, was used to measure the TNF/vinigrol interaction. The assay is similar to that of Imamura et al, J. Biol. Chem, 263, 10247-10253 (1988). More particularly, HL 60 cells (ATCC CCL 240) were grown in RPMI 1640 medium containing 10% foetal calf serum (FCS) and 1mM glutamine to a density of $1 \times 10^6$/ml and harvested by centrifugation at 150g for 10 minutes. Cells were resuspended to a density of $2 \times 10^7$/ml in RPMI 1640 containing 1% bovine serum albumin. $[^{125}I]$-TNF was diluted to 2.1nM in the above buffer containing 0.6% sodium azide. Nonspecific binding was estimated by measuring the binding in the presence of a 100 fold excess of unlabelled TNF. $[^{125}I]$-TNF, final concentration 700pM, vinigrol at the stated concentration and cells at a density of $5 \times 10^6$/ml were incubated in the above buffer for 2 hours at room temperature. The reaction was terminated by filtering onto a LKB filter mat (1205-401) followed by extensive washing with phosphate-buffered saline: The filter mat was counted for radioactivity to determine the quantity of bound $[^{125}I]$-TNF. The results are shown in Table 1 below.

TABLE 1

| Vinigrol inhibition of $[^{125}I]$-TNF-binding | |
|---|---|
| Vinigrol (μM) | Inhibition of $[^{125}I]$-TNF-binding (percent) |
| 310 | 100 |
| 31 | 12 |
| 3.1 | 8 |

EXAMPLE 2: TNF-cytotoxicity assay

TNF causes lysis at low concentrations in sensitive cell lines. A cell line, known to be sensitive to TNF, was challenged with the cytokine in the presence of vinigrol and the reduction in cell mortality (as measured by cell staining) quantified in a manner similar to the method of Matthews, *Immunology*, 48, 321 (1982). A measurement of the cytotoxicity of vinigrol at the various concentrations was also carried out.

L929 cells ($4 \times 10^4$/well) were incubated in RPMI 1640 medium containing 10ng/ml TNF, 0.05% lactalbumin hydrolysate and 1μg/ml actinomycin D plus the stated concentration of vinigrol overnight at 370° C. Cells were washed, fixed with methanol, stained with crystal violet and the cell density quantified by measuring absorbance at 590nm. The cytotoxicity of the samples was determined using the above method but excluding the TNF, in which experiments cell death would be due to the added vinigrol. Vinigrol inhibition of TNF-induced cytotoxicity is given in Table 2 below.

TABLE 2

| Inhibition of TNF-induced cytotoxicity | | |
|---|---|---|
| Vinigrol (μM) | Inhibition of TNF-induced cytotoxicity (percent) | Cytotoxicity vinigrol (percent) |
| 77.5 | 100 | 7 |
| 15.5 | 100 | 0 |
| 3.1 | 91 | 30 |

EXAMPLE 3: Pharmaceutical composition

Tablets, each weighing 0.15g and containing 25mg of vinigrol, can be manufactured as follows:

Composition (for 10000 tablets)

Vinigrol (250g)
lactose (800g)
corn starch (415g)
talc powder (30g)
magnesium stearate (5g).

The vinigrol, lactose and half the corn starch are mixed. The mixture is then forced through a sieve 0.5 mm mesh size. Corn starch (10g) is suspended in warm water (90 ml). the resulting paste is used to granulate the powder. The granulate is dried and comminuted on a sieve of 1.4 mm mesh size. Then the remaining quantity of starch, talc and magnesium stearate is added, carefully mixed and processed into tablets.

We claim:

1. A method for treating a patient suffering from endotoxic shock, which method comprises administering to the patient a thermapeutically effective amount of a compound selected from the group consisting of vinigrol and the pharmaceutically acceptable salts thereof.

2. A method for treating a patient suffering from inflammation, which method comprises administering to the patient a thermapeutically effective amount of a compound selected from the group consisting of vinigrol and the pharmaceutically acceptable salts thereof.